US012667453B2

(12) United States Patent (10) Patent No.: US 12,667,453 B2

Tepic et al. (45) Date of Patent: Jun. 30, 2026

(54) TREATMENT OF KNEE DISORDERS IN VETERINARY MEDICINE

(71) Applicant: Kyon AG, Zurich (CH)

(72) Inventors: Slobodan Tepic, Zürich (CH); Stephen Bresina, Davos (CH); Douglas Beck, Westminster, CO (US); Martin Kaufmann, Thornton, CO (US)

( * ) Notice: Subject to any disclaimer, the term of this patent is extended or adjusted under 35 U.S.C. 154(b) by 248 days.

(21) Appl. No.: 18/254,655

(22) PCT Filed: Nov. 24, 2021

(86) PCT No.: PCT/EP2021/082798

§ 371 (c)(1),
(2) Date: May 26, 2023

(87) PCT Pub. No.: WO2022/112313

PCT Pub. Date: Jun. 2, 2022

(65) Prior Publication Data

US 2024/0016594 A1 Jan. 18, 2024

Related U.S. Application Data

(60) Provisional application No. 63/118,800, filed on Nov. 27, 2020.

(51) Int. Cl.
| | |
|---|---|
| *A61D 9/00* | (2006.01) |
| *A61F 5/01* | (2006.01) |
| *A61F 5/058* | (2006.01) |

(52) U.S. Cl.
CPC .............. *A61D 9/00* (2013.01); *A61F 5/0111* (2013.01); *A61F 5/05841* (2013.01)

(58) Field of Classification Search
CPC ...... A61D 9/00; A61F 5/0111; A61F 5/05841; A61F 5/0585
See application file for complete search history.

(56) References Cited

U.S. PATENT DOCUMENTS

| | | | |
|---|---|---|---|
| 4,677,973 A | | 7/1987 | Slocum |
| 5,134,992 A | * | 8/1992 | Campbell ........... A61F 5/05841 602/23 |
| 5,441,015 A | | 8/1995 | Farley |
| 7,677,206 B1 | | 3/2010 | Southworth |
| 2002/0026135 A1 | | 2/2002 | Lowe |

(Continued)

FOREIGN PATENT DOCUMENTS

| | | |
|---|---|---|
| JP | 2001-512990 A | 8/2001 |
| JP | 2011-161065 A | 8/2011 |

(Continued)

OTHER PUBLICATIONS

Search Report and Written Opinion issued in International Application No. PCT/EP2021/082798, mailed on Feb. 28, 2022, 13 pgs.

(Continued)

*Primary Examiner* — Keri J Nelson
(74) *Attorney, Agent, or Firm* — Klarquist Sparkman, LLP

(57) ABSTRACT

The present invention provides an external brace, an orthosis, for treating disorders of joints in dogs and cats. The most relevant veterinary indication is a hock joint brace to treat cranial cruciate disease in dogs.

19 Claims, 6 Drawing Sheets

(56) References Cited

U.S. PATENT DOCUMENTS

2017/0354861 A1 * 12/2017 Pärssinen ........... A63B 71/1225
2020/0174448 A1 * 6/2020 Koop .................... B33Y 50/02

FOREIGN PATENT DOCUMENTS

JP       2012-055596 A    3/2012
WO       2015006818 A1    1/2015

OTHER PUBLICATIONS

Slocum and Slocum, "Tibial Plateau Leveling Osteotomy for Repair of Cranial Cruciate Ligament Rupture in the Canine", Vet. Clin. North Am. (1993), 23, pp. 777-795.
Slocum and Devine, "Cranial tibial wedge osteotomy: A technique for eliminating cranial tibial thrust in cranial cruciate ligament repair", J. Am. Vet. Med. Assoc. (1984), 184, pp. 564-569.
Tepic et al., "Biomechanics of the Stifle Joint", in Proceedings of the 1st World Orthopaedic Veterinary Congress, Munich, Germany (2002), pp. 189-190.
Boudrieau, "Tibial Plateau Leveling Osteotomy or Tibial Tuberosity Advancement?", Vet Surg. (2009), 38(1), pp. 1-22.
Meeson et al., "Soft-tissue injuries associated with cast application for distal limb orthopaedic conditions", Veterinary and Comparative Orthopaedics and Traumatology, 2011, 24 (02), 126-131.
Case et al., "Gastrocnemius Tendon Strain in a Dog Treated With Autologous Mesenchymal Stem Cells and a Custom Orthosis", Vet Surg 42(2013): 355-360.
Headrick, "A Description of the Movement of the Canine Pelvic Limb in Three Dimensions Using an Inverse Dynamics Method, and a Comparison of the Two Techniques to Surgically Repair a Cranial Cruciate Ligament Deficient Stifle" PhD disserations, University of Tennessee, 2012, 114 pgs.

* cited by examiner

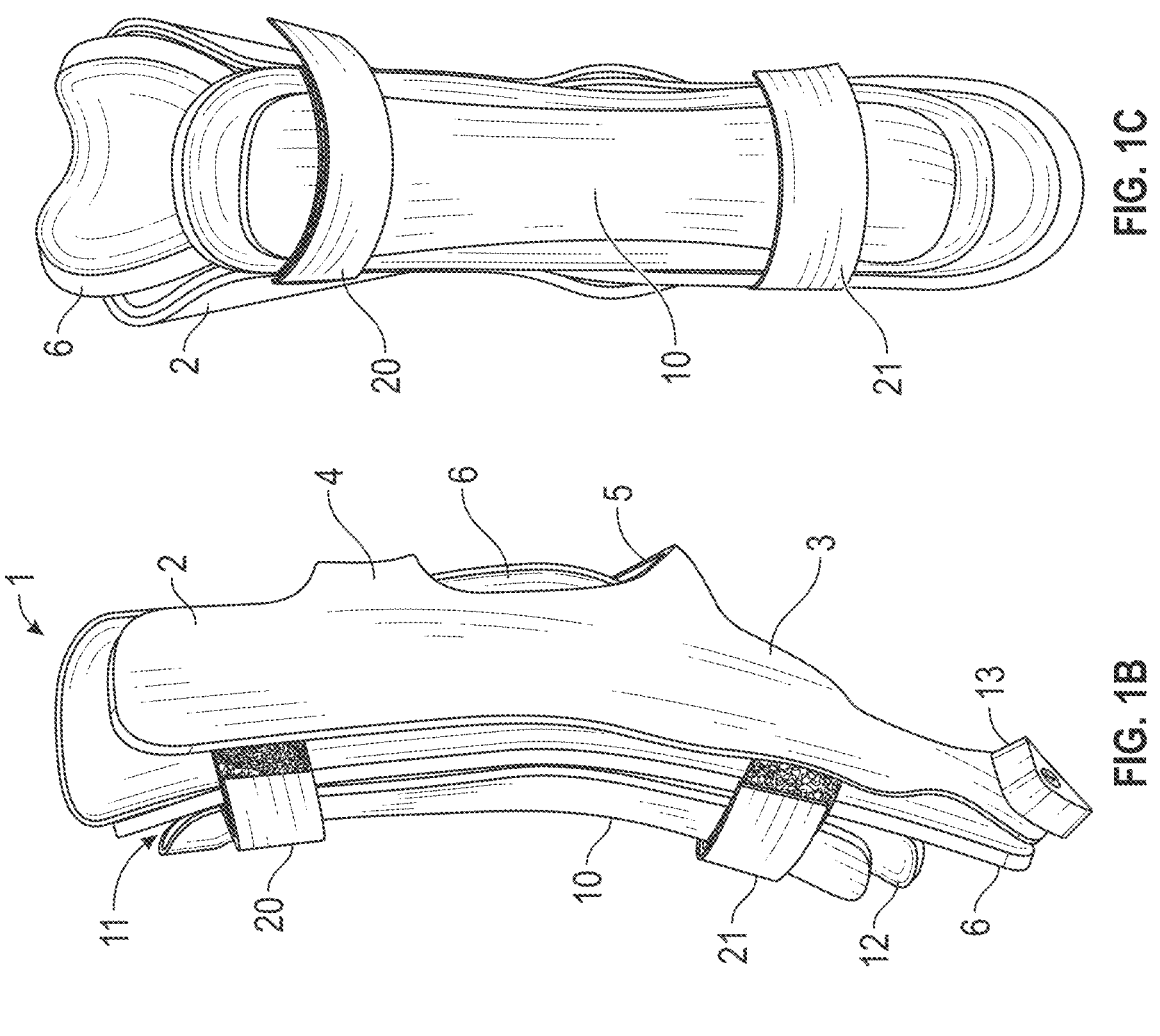
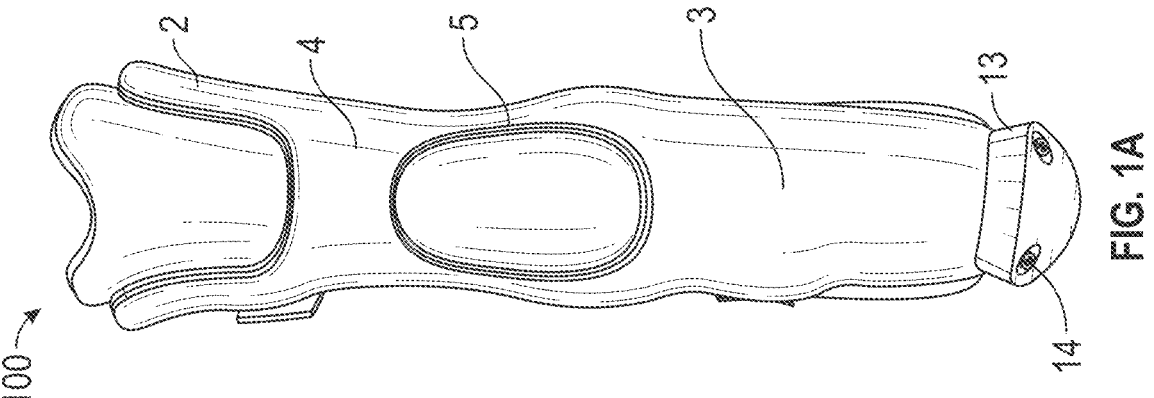
FIG. 1C
FIG. 1B
FIG. 1A

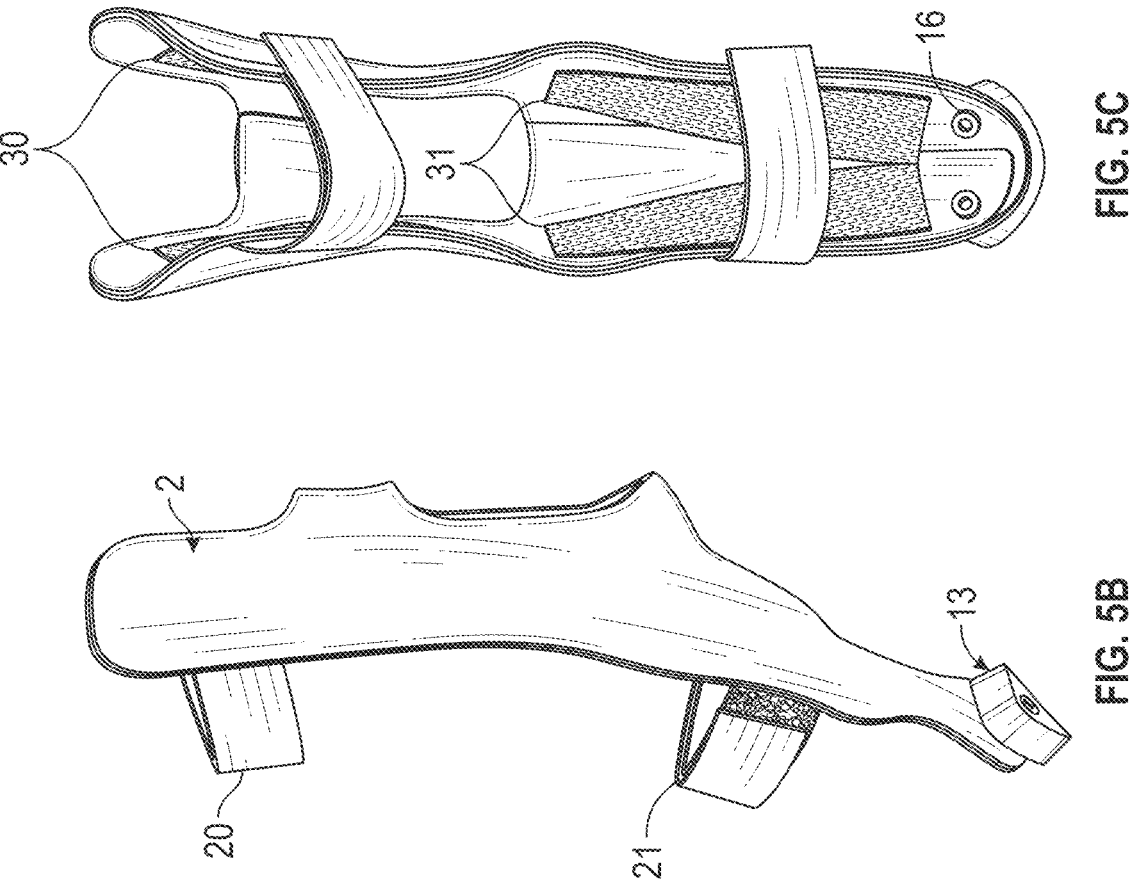
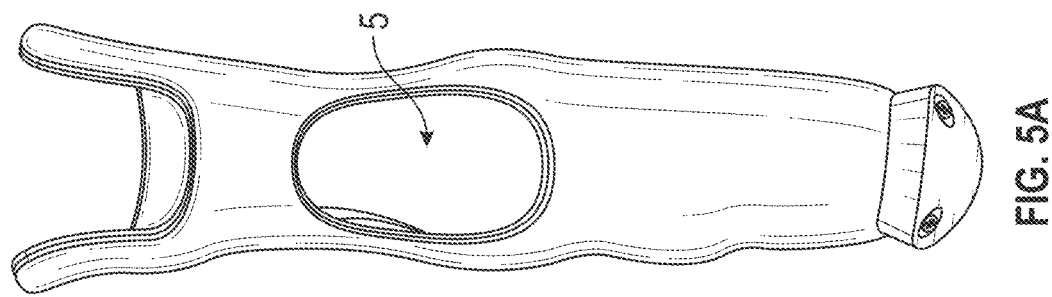
FIG. 5C
FIG. 5B
FIG. 5A

TREATMENT OF KNEE DISORDERS IN VETERINARY MEDICINE

CROSS REFERENCE TO RELATED APPLICATIONS

This application is a 35 U.S.C. 371 National Phase Entry Application from PCT/EP2021/082798 filed Nov. 24, 2021, which claims priority to and the benefit of U.S. Provisional Application No. 63/118,800, filed on Nov. 27, 2020, the disclosures of which are incorporated herein by reference in their entirety.

FIELD OF THE INVENTION

The present invention provides devices and methods for use in veterinary medicine, particularly for treating disorders of joints in animals such as dogs and cats. The most relevant veterinary indication is a hock joint brace to treat cranial cruciate disease. In particular, the present invention relates to devices and methods useful in treating disorders of the knee, termed the stifle in dogs, by holding the ankle, termed the hock joint, in extension.

BACKGROUND OF THE INVENTION

The anterior cruciate ligament (ACL) in the human knee joint, commonly called the cranial cruciate ligament (CrCL) in the canine stifle, is frequently torn in trauma. It also frequently fails, particularly in dogs, after a degenerative process of still unknown etiology.

In human orthopedics, standard procedures replace the failed ACL with an ACL allograft, or an autograft made from a part of the patient's own patellar tendon or a part of the fascia and tendon removed from the hamstring muscles. The procedure results in a stable knee, but the long-term performance of the knee is often unsatisfactory. Roughly, 75-90% of cases result in degenerative arthritis of the joint within 15 years of the procedure.

In dogs, the standard procedure involves either placement of an extra-capsular suture or performing one of several geometry-modifying surgical techniques. In the extra-capsular procedure, a suture is placed outside of the joint, usually on the lateral side, to approximate the function of the CrCL. The intention of the suture application is to provide stability of the joint for several weeks while waiting for fibrosis to occur around the joint. This fibrosis should then provide for long-term stability. However, the extra-capsular suture technique regularly results in failure. Degenerative arthritis of the joint, after a year or so, is the rule rather than the exception.

Attempts to replace the CrCL in the dog with an anatomically placed, intra-articular artificial ligament have also generally failed in spite of years of research and development of materials, anchor designs, and surgical techniques.

In surgical, geometry-modifying techniques, the tibia is cut, and a segment thereof is repositioned to change the geometry of the tibia and/or the joint in order to stabilize the stifle. Various techniques have been used, including tibial plateau leveling osteotomy (TPLO; see U.S. Pat. No. 4,677,973 and Slocum and Slocum, *Vet. Clin. North Am.* 23: 777-795, 1993), cranial closing wedge osteotomy (CWO; Slocum and Devine, *J. Am. Vet. Med. Assoc.* 184: 564-569, 1984), and tibial tuberosity advancement (TTA; Tepic et al., *Biomechanics Of The Stifle Joint*, in Proceedings of the 1st World Orthopaedic Veterinary Congress, Munich, Germany, pp. 189-190. 2002). Of the surgical approaches used in dogs, TTA seems to be associated with less morbidity and faster recovery, and it also provides immediate and durable stability to the joint (Boudrieau, *Vet Surg.*, 38(1): 1-22, 2009). Nevertheless, surgical complications are not uncommon with all these techniques. The most common is post-surgical damage to the medial meniscus caused by excessive, supraphysiological movement between the femur and the tibia.

Thus, there is a need of providing an effective treatment of a torn cranial cruciate ligament and further joint disorders in veterinary medicine.

SUMMARY OF THE INVENTION

The present inventors have performed in vitro experiments related to the treatment of stifle disorders and have found solid evidence that success is associated with reduction of the muscle force exerted on the stifle by gastrocnemius muscles. This goal is achieved by providing a novel external brace to create a biomechanical reaction force-modifying technique that replaces bandaging, which is difficult to apply consistently and is likely to cause soft tissue damage (Davidson, C., Arthurs, G. I. & Meeson, R. L. *Soft-tissue injuries associated with cast application for distal limb orthopaedic conditions*, Veterinary and Comparative Orthopaedics and Traumatology, 2011, 24 (02), 126-131).

The present invention relates to a device and method for conservatively treating a disordered joint, particularly a disordered knee in veterinary medicine. The device and method are useful for the treatment of an animal, e.g. a cat or a dog, and may involve applying a brace to the hock joint in extension. The disorder can be a partial or complete rupture of the cranial cruciate ligament (CrCL) due to any circumstance (e.g., due to trauma or a disease process). The device and the method of the invention can also be applied to treat other disorders at the hock joint, e.g., rupture of the Achilles tendon. The invention emerged from our in vitro study of the probable origin of cruciate disease in dogs, related to the imbalance of the hamstrings and gastrocnemius muscles.

The use of this brace is not restricted to cruciate disease cases, nor to the hock joint. There are many common orthopedic issues near the hock joint, e.g., rupture of the Achilles tendon, where the brace of the present invention has advantages over bandaging, casting or use of conventional braces (Case, J. B., et al. *Gastrocnemius Tendon Strain in a Dog Treated With Autologous Mesenchymal Stem Cells and a Custom Orthosis*, Vet Surg 42(2013): 355-360), which may restrict the movement of the joint but provide only a modest capacity to resist the bending moments. Of equal interest are applications to the front limbs, particularly to the carpal joint.

With the hock joint held in extension by the brace, the length of the gastrocnemius muscles is at its shortest. Even if the gastrocnemius muscles are innervated, the force that they can develop when kept short is very small. Further, when the reaction force vector is shifted closer to the hock joint, the bending moment is reduced resulting in less force acting upon the hock joint. To balance the extensors of the stifle (quadriceps) the dog will use hamstrings. With time, this leads to a permanent "reprogramming" favoring the use of hamstrings over gastrocnemius, which is well documented as a process of natural adaptation to cranial cruciate rupture. However, the use of the brace for several weeks to a few months, not only accelerates adaptation, but it protects the menisci from damage due to instability at the stifle. For favorable long-term outcomes, prevention of meniscal damage is essential.

In contrast to known stifle orthoses, the use of the brace according to the present invention is not mandatory for the rest of the life of the animal, e.g., dog. Once the muscle activity of the flexors and extensors is balanced, favoring the use of hamstrings over gastrocnemius, the brace can be removed. This period varies from case to case but is generally three to four months. The design of the inventive brace—in contrast to bandaging or casting—allows for easy removal and reapplication to the hock joint. It is also possible to modulate the restraint on the hock joint by simple re-adjustment of the length of the connections, which hold the two main components of the brace together.

Application of the brace of the current invention can also be performed as an adjunct procedure in, for example, geometry modifying surgeries (TPLO or TTA), or intra-articular suture implantations, in order to provide temporary protection of the implants and/or meniscus.

Another notable indication for the present invention is its application during the time prior to surgeries such as TPLO. In many specialized surgical clinics, the time from the first appointment to the surgery is frequently measured in months. This period presents a high risk for meniscal damage so that currently 50% or more of the dogs have torn their meniscus by the time of surgery. In addition to preventing meniscal damage prior to surgery, the application of the brace will also reduce the risks of post-surgical meniscal damage due to the same mechanism of promoting the use of hamstrings over gastrocnemius.

Accordingly, the present invention features devices and methods of treating a disordered animal stifle, particularly dog stifle by conservative means. As noted, the stifle injury may include a partially or fully ruptured cruciate ligament, the condition that we may refer to as cranial cruciate ligament disease (CrCLD).

A first aspect of the invention relates to a brace, which is adapted to be placed around a joint of an animal, e.g., around the carpal joint or the hock joint, particularly around the hock joint and more particularly around the hock joint of a dog, to limit its flexion-extension range of movement. The brace comprises two main rigid padded components connected by at least two sets of straps into a clam-shell-like construct.

A further aspect of the present invention relates to a method for the treatment of a joint disorder in an animal such as a dog, particularly to the treatment of a stifle disorder, and more particularly to the treatment of a cranial cruciate ligament disease of the stifle comprising applying to the joint a brace comprising two main rigid padded components connected by at least two sets of straps into a clam-shell-like construct.

In certain embodiments, the position of the hock joint when in the brace, is close to full extension of the hock. In gait, the hock joint angle moves through about 40 degrees. At the start of the stance phase, the angle is about 165 degrees; at 40% of the stance phase it drops to about 140 degrees; at the end of the stance phase it reaches about 180 degrees (Headrick, Jason, "*A Description of the Movement of the Canine Pelvic Limb in Three Dimensions Using an Inverse Dynamic Method, and a Comparison of the Two Techniques to Surgically Repair a Cranial Cruciate Ligament Deficient Stifle*" PhD diss, University of Tennessee, 2012). The brace of the invention can be made for holding the hock in positions with different angles, preferably in positions wherein the angle is between about 145 and about 170 degrees, and most preferably in a position wherein the angle is about 155 degrees. Preferably, the padding and/or the compliance of the construct are adapted for allowing about 5 to about 10 degrees movement at the hock joint within the brace.

In certain embodiments, the two main components of the brace are shaped to fit caudo-plantar and cranio-dorsal aspects of the hind limb in a dog or cat, particularly in a dog.

In particular embodiments, the first main component is shaped to fit the caudo-plantar aspect of the metatarsal bases. The first main component may comprise a hard shell having a distal part and a proximal part. The distal part may be concave, formed to support the metatarsals, creating a contact point to the ground e.g., via a rubber pad caudal to the central paw pad. The proximal part may wrap around the caudal aspect of the distal tibia, distal to the insertion points of the hamstrings along the medial aspect of the proximal tibia. In certain embodiments, the hard shell of the caudo-plantar component may be provided with an opening at the position of the calcaneus. The inner side of the hard shell of the first main component may be covered with a padding, e.g., a foam padding such as neoprene foam. The padding may establish contact to the distal caudal gastrocnemius tendon and proximal aspect of the calcaneus.

In certain embodiments, the second main component is shaped as a cranio-dorsal cover of the joint, e.g., the hock joint. The second main component may comprise a hard shell having proximal surface and a distal surface. The proximal surface may be shaped to fit the tibial crest located on the proximal cranial tibia and the tibial tuberosity. The transition zone of the cranial cover may be shaped to eliminate contact to the cranial tibialis tendon located on the distal tibia and the insertion of the cranial tibialis tendon located on the proximal cranial hock. The distal surface of the cranial cover may be shaped to fit the curvature of the metatarsals and alleviate contact and pressure upon the digital extension tendons. Additionally, the distal end of the cranial cover may terminate at the distal surface of the metatarsals. The inner side of the hard shell of the second main component may be covered with a padding, e.g., a foam padding such as neoprene foam.

In certain embodiments, the straps are positioned at the proximal and the distal aspects of the two main components of the brace. The length of the straps may be adjustable. In certain embodiments, the straps are hook and loop fastener bands. The location of the proximal and distal straps purposely establishes a connection between the first and the second main component resulting in the creation of the 4-point bending control system.

In certain embodiments, the main rigid padded components comprise a shell of a rigid material and a padding adapted to align with the shell. The rigid material of the shells may be a thermoplastic material, for example a composite of wood and a thermoplastic polymer, e.g., a biodegradable polymer, such as Woodcast.

In certain embodiments, the distal end of the hard shell of the caudo-plantar component comprises a removable rubber pad, wherein removable rubber pads made in several different lengths may be provided.

The brace of the invention may be made in several sizes for animals, particularly for dogs, e.g., from toy to giant breeds.

BRIEF DESCRIPTION OF THE DRAWINGS

FIG. 1 shows orthogonal views of an inventive brace.

FIG. 5 is a photograph of the brace main component without padding.

DETAILED DESCRIPTION

Figure 2:
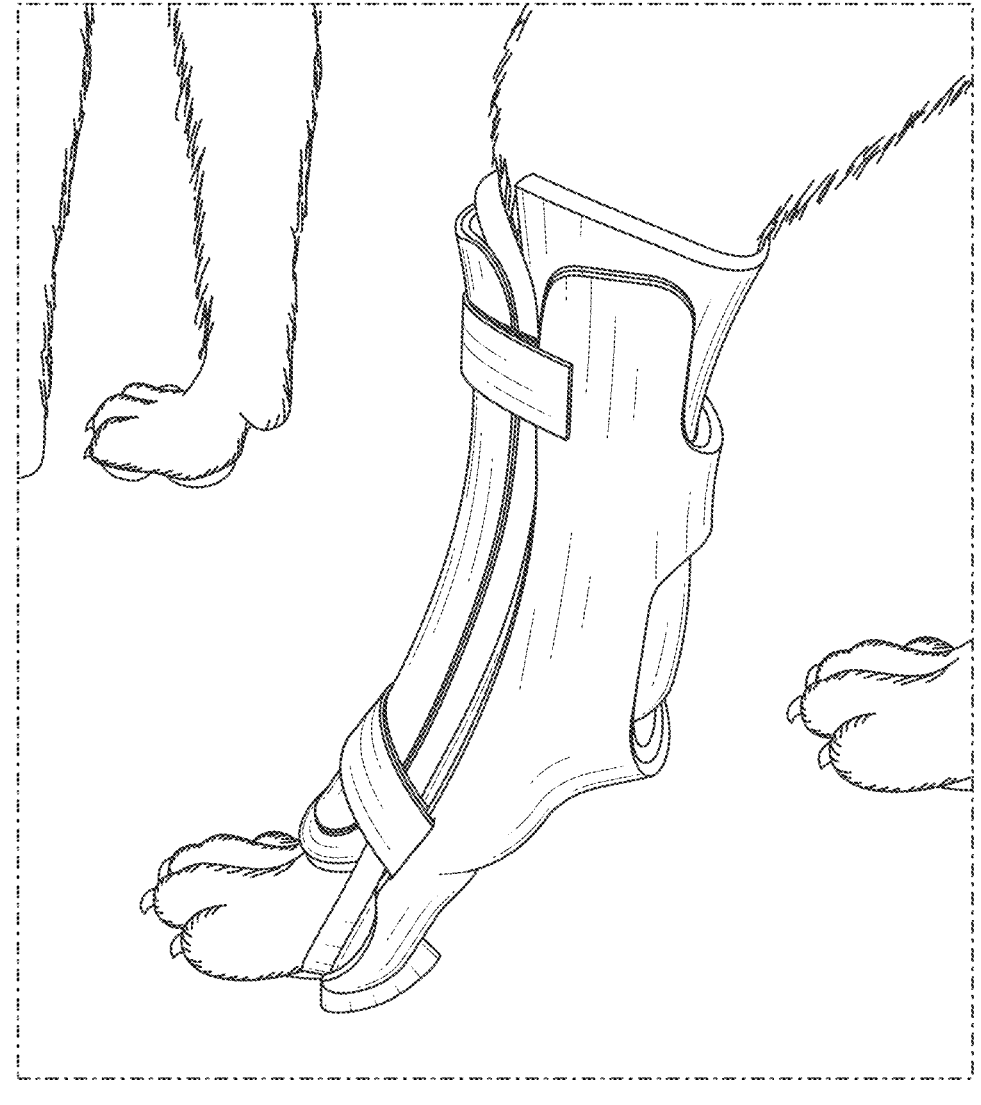
FIG. 2 is a photograph of the brace on the hock of a dog.

This invention is based, at least in part, on in vitro experiments and clinical observations that have helped us identify the fundamental causes of the slow process of degradation of the CrCL in the dog. Our experimental work with dog cadavers has shown a strong destabilizing effect of the gastrocnemius muscles. The force that these muscles exert can be greatly reduced by shortening the muscle working length by extending the hock joint. Since the dog is free to use its distal limb, the moment exerted on the hock joint due to ground reaction must be transferred to the tibia, which defines the first of two main mechanical functions of the brace—resisting the moment by reactive forces to the tibia shaft and the metatarsals. In mechanical terminology, this is referred to as four-point-bending. To reduce the magnitude of the force acting upon the hock joint resulting in gastrocnemius muscle contraction, the second main mechanical function of the brace modifies the point of contact to the ground and shifts the reaction force vector closer to the hock joint thereby reducing the flexion moment, which in turn reduces the magnitude of the force that the gastrocnemius muscle attempts to resist through muscle contraction. In mechanical terminology, this is referred to as ground reaction force vector alignment.

Our results are generally applicable in veterinary medicine, not only for dogs, but also for other animal species such as cats.

FIG. 1 shows a photograph of the brace 100 in orthogonal views: (a) is the caudal view; (b) is the lateral view; (c) is the cranial view. The brace is composed of two rigid padded components connected by at least two sets of straps into a clam-shell-like construct covering the caudo-plantar and cranio-dorsal aspects of the distal hind limb.

The first main component 1 of the brace 100 is a hard shell 2 shaped to fit the caudo-plantar aspect of the metatarsal bases of the distal hind limb. The purpose of the specific shape of the caudo-plantar component is to disperse forces over a larger area of soft tissue to reduce soft-tissue injury. Shell 2 may be formed from a thermoplastic material. The distal part 3 of the hard shell 2 may be concave, formed to support the metatarsals, creating a contact point to the ground e.g., via rubber pad 13 caudal to the central paw pad. The purpose of contacting the ground caudal to the central paw pad is to modify the ground reaction force vector alignment beneficially closer to the hock joint to reduce the magnitude of the hock joint flexion moment. The proximal part 4, wraps around the caudal aspect of the distal tibia, distal to the insertion points of the hamstrings along the medial aspect of the proximal tibia. The purpose of part 4 location is to eliminate hamstring contact to the proximal caudal edge of the brace 100 that results in soft-tissue sores and distal brace migration leading to destabilizing of the hock joint. In the transition zone from the proximal part 4 to the distal part 3 of the hard shell 2, there is an opening 5 corresponding to the anatomical structure of calcaneus. The purpose of opening 5 is to remove the risks of pressure sores of the soft tissue covering the calcaneus. Padding 6 covers the inner side of the brace component 1. The padding establishes contact to the distal caudal gastrocnemius tendon and proximal aspect of the calcaneus intentionally to create brace 100 purchase and suspension to the pelvic limb and resisting the device distally migrating off the limb resulting in complete destabilization.

The second main component of brace 100 is a tongue-shaped cranio-dorsal cover 10 of the hock joint. It may also be formed from a thermoplastic material. The proximal surface of the cranial cover 10 is shaped to fit the tibial crest located on the proximal cranial tibia and the tibial tuberosity. The purpose of this shape is to eliminate soft-tissue wounds commonly associated with bandages at this location of the pelvic limb. The transition zone of the cranial cover 10 is shaped to eliminate contact to the cranial tibialis tendon located on the distal tibia and the insertion of the cranial tibialis tendon located on the proximal cranial hock. The purpose of this transition zone shape is to reduce soft-tissue injury to the skin covering the tendon and eliminate direct tendon pressure resulting in pain. The distal surface of the cranial cover 10 is shaped to fit the curvature of the metatarsals and alleviate contact and pressure upon the digital extension tendons. Additionally, the distal end of the cranial cover 10 terminates at the distal surface of the metatarsals purposely so that the digits are not restricted during gait. Padding 12 covers the backside of shell 11.

The main components 1 and 10 of the brace 100 are connected by two sets of straps 20 and 21 at the proximal and the distal aspects of the brace. Each set of straps may be made of 3 strips of hook and loop fastener bands making two pairs of connections. One pair connects one side of component 1 to component 10, and the other pair the other side of component 1 to component 10. In this manner, the position of the tongue 10 is fixed relative to the main component 1 both in a sideways position and in distance from proximal to distal. The location of the proximal and distal straps purposely establishes the connection between component 1 and component 10 resulting in the creation of the 4-point bending control system. The rubber pad 13 is fixed to the distal end of the shell 2, e.g., by two screws 14.

FIG. 2 shows the brace 100 applied to the hock joint of a dog. This is a small brace on a dog of about 18 kg bodyweight. Six sizes of the brace from XX-Small to X-Large may cover dogs from toy to giant breeds.

Figure 3:
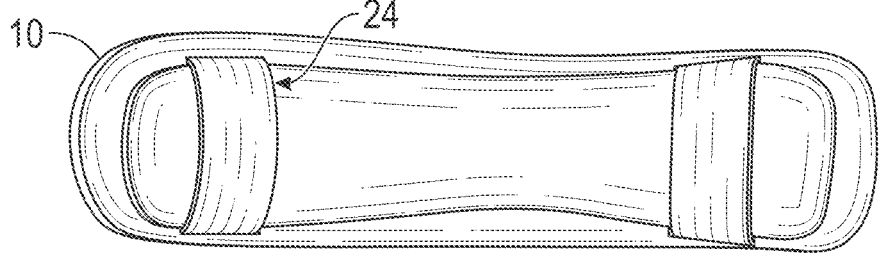
FIG. 3 is a photograph of the brace with two main components separated.
Figure 3:
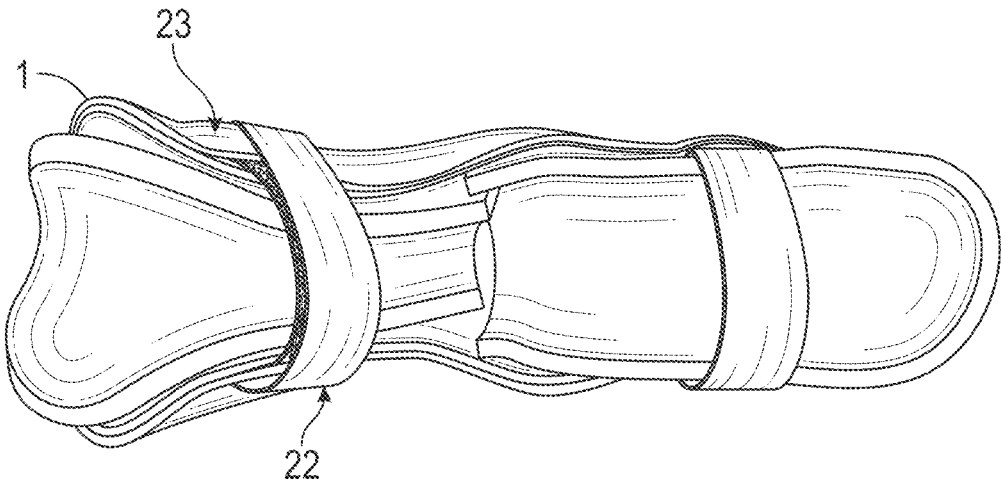

FIG. 3 shows the two components of the brace separated. The hook and loop fastener band 22 of the proximal set 20 of straps is a loop-type. Band 23 is loop-type on the inside and hook-type on the outside. Band 24 covers the full width of tongue 10 and is hook-type. Fixation of the tongue component 10 to the main component 1, is done by first affixing band 23 to band 24, followed by affixing band 22 over band 23. The bands of hook and loop fastener are fixed to the brace component between the two layers of the hard shell 2.

Figure 4:
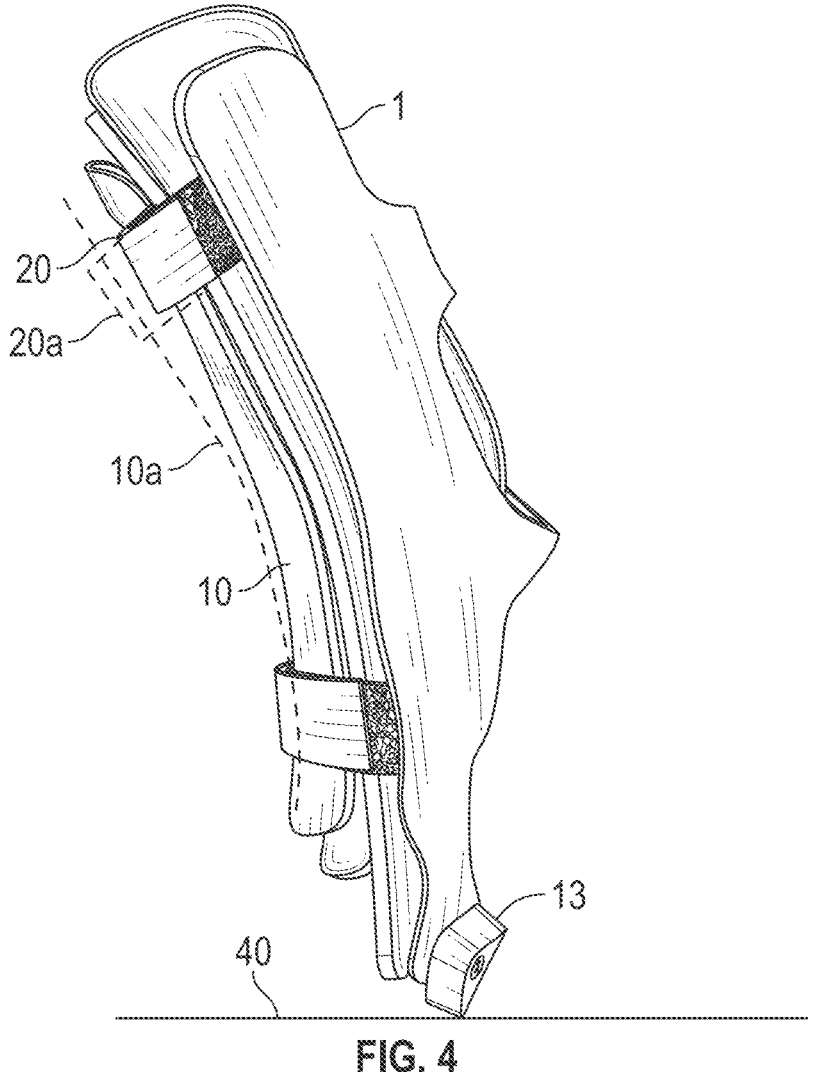
FIG. 4 is a photograph of the brace configured to hold the hock joint in full extension.

FIG. 4 shows the brace in its most flexion-restraining position with the tongue 10 fully pulled in towards the main component 1. The angle of full extension of the hock joint varies between dogs of different breeds and between individual dogs of the same breed. This variability can be accommodated by the length of the straps and the angle of the bend of the tongue 10. It is also possible to modulate the restraint on the hock joint range of flexion/extension by bending the tongue 10 into the shape shown schematically by dashed line 10a. The straps 20 can be lengthened as shown by 20a. This now allows for an increased range of hock joint flexion/extension movement by about 5 to 10 degrees and may be desired in the course of the joint immobilization during typically 10 to 16 weeks, most commonly about 12 weeks. The position of the brace shown is typical for the mid-stance of the gait. The pad 13 contacts the ground through most of the stance phase, protecting the main component 1 of the brace from wear and tear and also reducing the impact loading that would result from the hard shell hitting the ground.

FIG. 5 shows orthogonal views of the hard shell component 2 of the brace without internal padding. For the hard shell components, preferably a thermoplastic material, most preferably a composite of wood and a bio-degradable polymer, e.g. Woodcast (Onbone Oy, Finland) is used. This makes it possible to fine-tune the hard shells to the individual anatomical features by heating the brace to an elevated temperature, e.g., of about 65° C., and bending the shells into the desired shape. Shell 2 and the tongue 10 may be formed from multiple layers of material, e.g., Woodcast, to provide the stiffness and the strength needed. Two layers of 2 mm in thickness each with the overlap along the midline of the brace are usually sufficient. Hook and loop fastener bands 30 and 31 are glued to the inner side of the shell 2 to provide anchoring for the padding 6 made from preferably neoprene foam. Flanged nuts 16 at the distal end of the shell accept screws 14 for affixing of rubber pad 13.

Figure 6:
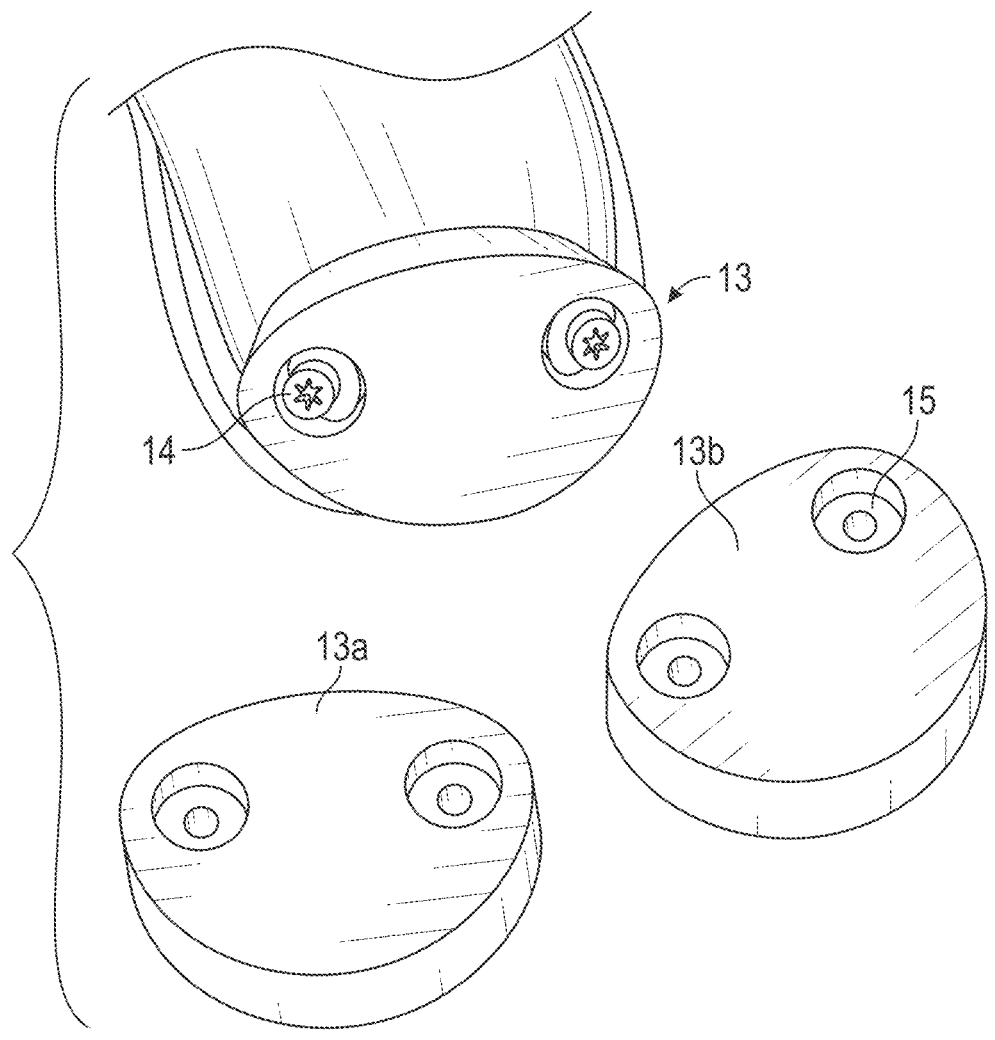
FIG. 6 is a photograph of the ground-contacting rubber pads.

FIG. 6 shows the distal end of the brace with exchangeable rubber pads 13 affixed to the shell 2 by two screws 14. The pads are made in several lengths from the tip of the pad to the fixation screws, shown here as 13*a* and 13*b*. Selection of the appropriate pad allows for sharing of the ground reaction between the brace and the paw. The pad also protects shell 2 from wear and tear against the ground and softens the contact impact on hard surfaces. Metal washers 15 are inserted at the bottom of the screw head recesses to allow for proper screw tightening into flanged nuts 16.

Alternative, a commonly used material for hard orthoses is polypropylene, which requires a much higher temperature for molding.

Having disclosed at least one embodiment of the present invention, variations will be understood by one of ordinary skill in the art. Such adaptations, modifications, and improvements are considered part of the invention.

What is claimed is:

1. A brace adapted for application to a hock joint of an animal, the brace comprising a first main component comprising a hard shell and a padding and a second main component comprising a hard shell and a padding, wherein the first and the second main components are connected by at least two sets of straps into a clam-shell-like construct configured to surround the joint thereby limiting its flexion-extension range of movement, wherein the first main component is adapted to fit a caudo-plantar aspect of a distal hind limb of the animal and the second main component is adapted to fit cranio-dorsal aspects of the distal hind limb, and wherein the brace is adapted to hold the hock joint angle close to full extension, wherein a distal end of the hard shell of the first main component comprises a removable rubber pad.

2. The brace according to claim 1, wherein the hock joint angle is in a range from 145 to 170 degrees.

3. The brace according to claim 1, which is adapted for application to the hock joint of a dog.

4. The brace according to claim 1, wherein the hock joint angle is about 155 degrees.

5. The brace according to claim 4, wherein the padding allows for movement within the brace in a range from 5 to 10 degrees.

6. The brace according to claim 1, wherein the hard shell of the first main component is provided with an opening at the position of the calcaneus.

7. The brace according to claim 1, wherein the length of the straps is adjustable.

8. The brace according to claim 1, wherein the straps comprise at least one hook and loop fastener band set comprising a plurality of hook and loop fastener bands.

9. The brace according to claim 8, wherein the straps comprise at least one hook and loop fastener band set comprising three hook and loop fastener bands.

10. The brace according to claim 1, wherein the hard shell of the first main component and/or the hard shell of the second main component is made from a thermoplastic material.

11. The brace according to claim 10, wherein the thermoplastic material is a composite of wood and a biodegradable polymer.

12. The brace according to claim 1, wherein the removable rubber pad is provided in several different lengths.

13. The brace according to claim 1, adapted to treat cranial cruciate ligament disease of the stifle.

14. The brace according to claim 1, made in several sizes for animals.

15. A method for treatment of a joint disorder in an animal, the method comprising applying to a hock joint a brace comprising a first main component comprising a hard shell and a padding and a second main component comprising a hard shell and a padding, wherein the first and the second main components are connected by at least two sets of straps into a clam-shell-like construct around the joint thereby limiting its flexion-extension range of movement, wherein the first main component is adapted to fit a caudo-plantar aspect of a distal hind limb of the animal and the second main component is adapted to fit cranio-dorsal aspects of the distal hind limb, and wherein the hock joint angle is close to full extension.

16. The method according to claim 15, wherein the disorder is stifle disorder, and the brace is applied to the hock joint.

17. The method according to claim 16, wherein the stifle disorder is a cranial cruciate ligament disease of the stifle.

18. The method according to claim 15, wherein the animal is a dog.

19. The method according to claim 15, wherein the hock joint angle is in the range from 145 to 170 degrees.

* * * * *